United States Patent [19]

Mukasa

[11] 4,331,132

[45] May 25, 1982

[54] ANGIOSCOPE

[75] Inventor: Shizuo Mukasa, Hachioji, Japan

[73] Assignee: Olympus Optical Company Ltd., Tokyo, Japan

[21] Appl. No.: 136,097

[22] Filed: Mar. 31, 1980

[30] Foreign Application Priority Data

Apr. 5, 1979 [JP] Japan .................................. 54/41348

[51] Int. Cl.³ .......................... A61B 1/06; A61B 5/02
[52] U.S. Cl. ....................................... 128/6; 128/145; 128/691; 356/39; 73/861.05
[58] Field of Search ................... 128/4, 666, 691, 699, 128/745, 774; 364/415, 416; 358/105, 107; 354/62; 351/7; 356/39; 73/861.05

[56] References Cited

U.S. PATENT DOCUMENTS 3,777,738 12/1973 Sugita et al. .......................... 128/745
4,166,695 9/1929 Hill et al. .......................... 128/691 X
4,257,688 3/1981 Matsumura .............................. 351/7

*Primary Examiner*—Stephen C. Pellegrino

*Attorney, Agent, or Firm*—Stevens, Davis, Miller & Mosher

[57] ABSTRACT

In an angioscope for observing the conditions of a blood vessel, a microscope comprises an optical system for forming a blood vessel or vascular image illuminated by a reflecting illumination device on a camera tube; a monitor device for magnifying and projecting the vascular image formed on the camera tube onto the screen of a television receiver by known magnification; a size measuring means for projecting on the screen of the monitor a size measuring index with magnification proportional to the magnification of the vascular image by utilizing the steps of superimposing the index upon the vascular image projected on the screen of the television monitor, relatively displacing the index from the vascular image, and measuring a size of a blood vessel from a size of the index and the magnification; and/or a flow rate arithmetic monitor device for calculating a flow rate of the blood flowing through the blood vessel by detecting the time required for movement of a red blood cell in the blood vessel projected on the screen of the television monitor over a predetermined distance on the screen of the television monitor.

16 Claims, 8 Drawing Figures

ANGIOSCOPE

BACKGROUND OF THE INVENTION

The present invention relates to an angioscope or vascular microscope for observing the conditions of blood vessel.

In a progress observation and diagonosis of diabetes mellitus, cerebral apoplexy or the like it has been desired to develop an angioscope capable of observing the color and shape of blood vessel or the conditions of a blood flow (whether or not red blood-corpuscles flow in regular order or whether or not the clot is a single body) in a noncontiguous manner.

SUMMARY OF THE INVENTION

It is an object of the present invention to provide an angioscope capable of effectively observing the color and the shape of blood vessel or the conditions of a blood flow in non contacted manner without requiring any particular treatment with a simple construction.

According to the present invention an angioscope for observing the conditions of blood vessel comprises an optical system for forming a blood vessel or vascular image illuminated by a reflecting illumination device on a camera tube; a monitor means for magnifying and projecting the vascular image formed on the camera tube onto the screen of a television receiver by known magnification; a size measuring means for projecting on the screen of the monitor a size measuring index with magnification in certain relation to the magnification of the vascular image by superimposition upon the vascular image projected on the screen of the television mnitor, relatively displacing the index from the vascular image, and measuring a size of a blood vessel from a size of the index and the magnification; and/or a flow rate arithmetic monitor means for calculating a flow rate of the blood flowed through the blood vessel by detecting the time required for moving a red blood cell in the blood vessel projected on the screen of the television monitor over a predetermined distance on the screen of the television monitor.

The size measuring index consists of two arrows arranged to face each other in a straight line and separated by a certain distance on the screen of the television receiver.

The size measuring means comprises a frame memory, the position and the size of the index projected on the screen of the television receiver in synchronized with the video output of the camera tube are made changeable, and these position and the size of the index and the magnification of the vascular image are controlled so as to coincide the index dimension with the magnification thereby to calculate an actual dimension of blood vessel from these index dimension and the magnification.

The flow rate arithmetic means comprises a measuring terminal having two light receiving elements arranged to separate by a certain distance, the measuring terminal is contacted onto the vascular image projected on the screen of the television receiver to detect a time required for flowing between the light receiving elements the red blood cell flowing in the blood vessel, thereby to calculate an absolute value and a changed value of flow rate of the blood from the required time, the distance between these light receiving elements and the magnification of the vascular image.

As a suitable portion for observing blood vessels in organism or living body in noncontiguous manner there is a capillary vessel on pleura.

In a preferable embodiment according to the present invention use is made of a fundus camera which is improved by making a conventional fundus camera high magnification to extend and observe capillary vessel at pleura portion as in a common microscope, the capillary vessel or vascular image of pleura portion observed by adding a magnifying projection device consisting of a color camera tube and a color television receiver to the fundus camera, is focused on the color camera tube so as to magnify and project it on the screen of the color television receiver and then the size measuring means and flow rate arithmetic monitor means are added to measure the size of blood vessel and the flow rate of the blood.

DESCRIPTION OF THE PREFERRED EMBODIMENTS

Figure 1:
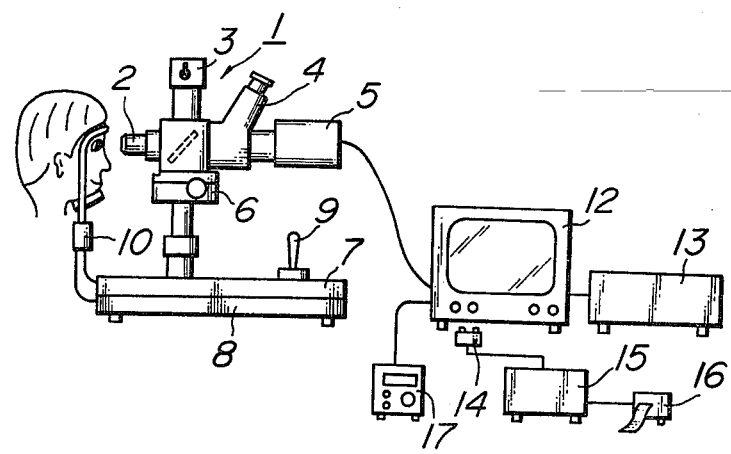
FIG. 1 is a diagram showing a construction of one embodiment of an angioscope according to the present invention.

Referring now to FIG. 1 one embodiment of an angioscope according to the present invention will be explained.

The angioscope has a microscope device 1 comprising an objective lens 2, a reflecting illumination device 3, an observation portion 4 and a color camera tube 5. This microscope device 1 is mounted to an X-Y moving table 7 through a horizontal fine adjustment 6 and a vertical drive means (not shown). The vertical drive means comprises a fine adjustment and a rack and pinion adjustment. The X-Y moving table 7 is mounted on a stationary base 8 to make the microscope device 1 movable on a horizontal plane by operation of a rack and pinion adjustment. The stationary base 8 is also provided with a face fixing member 10. The objective lens 2 is so constructed that any one of various magnifications (the range of 100–150 times, preferably) can be selected.

Figure 2:
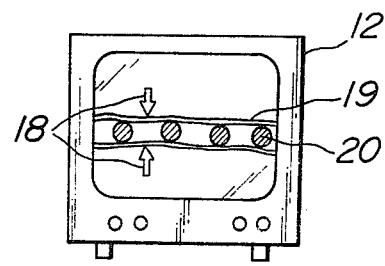
FIG. 2 is a diagram showing an image of blood vessel and a size measuring index which are displayed on a color television receiver shown in FIG. 1.

The video output of the color camera tube 5 is supplied to a color television receiver 12 and a video recording device 13 to magnify and project an image of capillary vessel at a pleura portion focused on a focal plane of the camera tube onto the screen of the color television receiver and to record it in the video recording device 13. In order to measure flow rate of the blood by detecting flow rate of red blood cell in the blood vessel displayed on the screen of the color television receiver 12, use is made of a flow rate arithmetic unit 15 having measuring terminal 14 so as to record flow rate of the blood calculated by the unit 15 on a data printer 16. The flow rate arithmetic unit 15 comprises two light receiving elements provided to the measuring terminal 14 as described later on to calculate an absolute value and a changed value of flow rate of the blood from a distance between two light receiving elements, a magnification of the blood vessel or vascular image, and a time required for flowing between the light receiving elements red blood cell flowing in the blood vessel, the required time being measured by contacting the measuring terminal 14 to the blood vessel image displayed on the screen of the color television receiver 12. The receiver 12 is also connected to a size measuring device 17 for measuring the size or dimension of the blood vessel. The measurement of the blood vessel size is performed by displaying an index for measuring the size of the displayed blood vessel image on the screen of the color television receiver 12 to superimpose it thereon and obtaining the dimension of the blood vessel from the size of the index and the magnification of the blood vessel image. The size measuring device 17 comprises a frame memory for storing an image signal of the index 18 displayed on the screen of the color television monitor 12 under the control of synchronizing signals of the video signal form the camera tube 5. As shown in FIG. 2, the index 18 is consisting of two arrows directing oppositely along a vertical line. A distance between the arrow points can be adjusted at will by means of a control knob and a position of the arrows on the screen can be also changed by handling a joy stick. By suitably adjusting the control knob and joy stick, the blood vessel is sandwiched between the arrow tips as shown in FIG. 2. Then a distance between the arrow tips D can be detected by counting the number of scanning lines situating between the arrow tips. Further, a magnitude m of the blood vessel image is known from a magnitude of an objective lens provided in the camera tube 5 and a ratio of a raster size of a target in the camera tube and a raster size on the screen of the monitor 12. Then an actual size d of the blood vessel can be measured from d=D/m. The actual size of the blood vessel is then displayed and/or recorded. In FIG. 2, red blood cells moving along the blood vessel 19 are denoted by a reference numeral 20.

Figure 5:
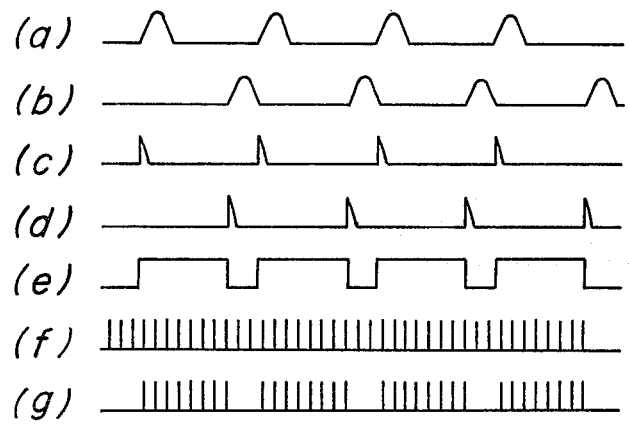
FIGS. 5a–5g are waveform charts showing signals at various portions in the circuit shown in FIG. 3.
Figure 3:
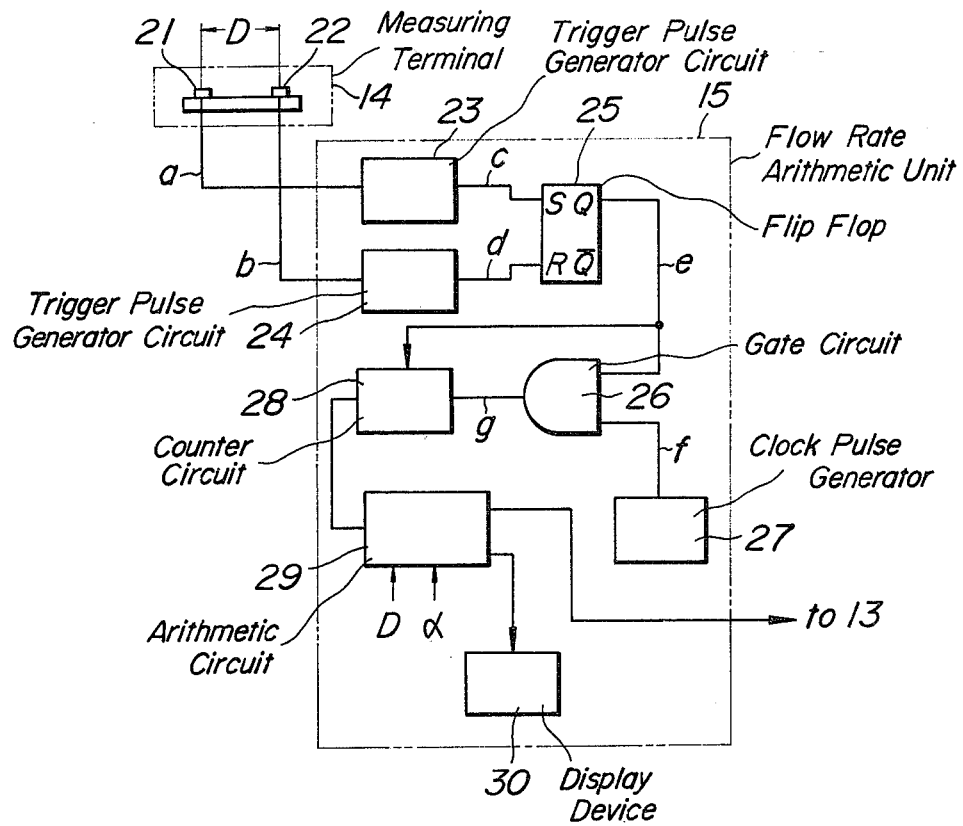
FIG. 3 is a block diagram showing a circuit construction of one embodiment of flow rate arithmetic unit shown in FIG. 1.
Figure 4:
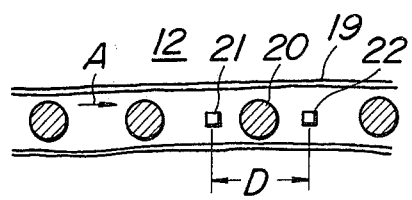
FIG. 4 is a diagram showing mode of flow rate measuring obtained at a measuring terminal shown in FIG. 3.

The flow rate arithmetic unit 15 having the measuring terminal 14 is explained in detail with reference to FIGS. 3, 4 and 5. The measuring terminal 14 is provided with two light receiving elements 21 and 22 displaced at intervals of a certain distance D and these elements 21 and 22 are contacted to the blood vessel image 19 displayed on the color television receiver 12 in the direction of blood flow shown by an arrow A thereby to detect the red blood cell 20 passing between these light receiving elements 21 and 22. The outputs of the light receiving elements 21 and 22 are shown in FIGS. 5a and 5b. These outputs of the elements 21 and 22 are supplied to trigger pulse generator circuits 23 and 24, respectively, to form trigger pulses shown in FIGS. 5c and 5d, respectively by means of the leading edge of output pulses of the elements 21 and 22 and these trigger pulses are supplied to the set and the reset terminals of a set-reset flip flop 25, respectively. The Q output of the flip flop 25 therefore changes as shown in FIG. 5e every time the red blood cell 20 passes between the light receiving elements 21 and 22. The Q output is supplied to a gate circuit 26 to gate the output of a clock pulse generator 27 for generating clock pulses of a certain period shown in FIG. 5f thereby to supply these clock pulses to a counter circuit 28 selectively. The counter circuit 28 receives clock pulses only when the Q output of the flip flop 25 is a value of logic level "1" as shown in FIG. 5g so that a time t required for passing through the red blood sell 20 between the light receiving elements 21 and 22 can be obtained by counting the number of the clock pulses. The The output of the counter circuit 28 showing the required time t is supplied to an arithmetic circuit 29 to obtain the flow rate v of the blood from the distance D and the magnification $\alpha$ of the blood vessel image 19 based on the calculation of following formula $v=D/(\alpha \cdot t)$. The signals showing the flow rate v of the blood thus obtained are supplied to a data printer 13 to record these signals and supplied to a display device 30 to display the flow rate v of the blood.

Figure 6:
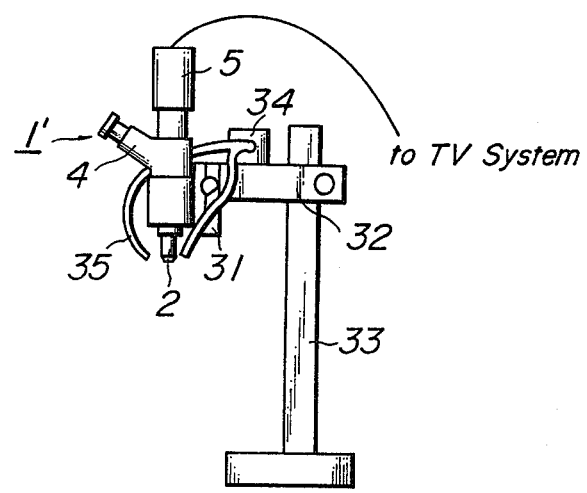
FIG. 6 is a diagram showing construction of essential portion of another embodiment of an angioscope according to the present invention.

FIG. 6 is a diagram showin a construction of another embodiment of an angioscope according to the present invention. In this embodiment particularly in order to observe the condition of the blood of a patient lying down on a bed the optical axis of the angioscope is vertically arranged and the reflecting illumination is utilized with a light guide. These two points are only differ from the angioscope shown in FIG. 1 so that FIG. 6 shows only the microscope portion and a television monitor portion is omitted. The angioscope 1' comprises the objective lens 2, the observation portion 4 and the color camera tube 5 and is attached to an elevating member 32 through a vertical fine adjustment 31. The elevating member 32 is rotatably mounted to a stand 33 and movably held in the vertical direction. An illumination source 34 is arranged on or around the elevating member 33 and constructed to reflectively illuminate the portion to be observed by the objective lens 2 through a light guide 35. The light guide 35 can be branched to two at the exit end or formed into one or a bundle.

As described above, according to the invention, it becomes possible to obtain a vascular microscope for effectively observing the shape and the color of a blood vessel or the conditions of a blood flow in a noncontiguous manner with a simple construction.

Figure 7A:
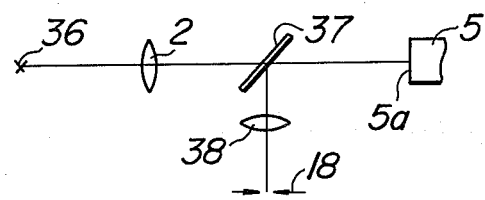
FIGS. 7a and 7b are diagrams showing two display modes of another size measuring index.
Figure 7B:
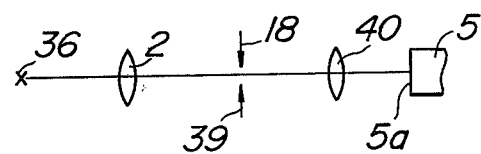

The present invention is not limited to the above embodiment but can be variously changed or modified. For example, it is possible to provide either one of the flow rate arithmetic device 15 and the size measuring device 17, if necessary. Moreover, the flow rate arithmetic device 15 can electronically set a given distance D on the screen of the receiver 12 instead of using the measuring terminal 14 having two light receiving elements 21, 22, to detect the time required for passing the red blood cell 20 through the distance D thereby to purely electronically obtain the flow rate v of blood. Furthermore, the size measuring index 18 can be constructed to form an image of the index 18 with magnification having a certain relation to the magnification of the blood vessel image 19 superimposed on the focal plane of the camera tube 5 other than the system for projecting an image on the screen of the receiver 12 in synchronization with the image output of the camera tube 5. That is, as shown in FIG. 7a, a half-mirror 37 is provided between the objective lens 2 and a focal plane 5a of the camera tube 5 in an optical system of a subject to be measured 36 having the objective lens 2, and the index 18 is formed into an image on the focal plane 5a through the other objective lens 38 and the half-mirror 37. Furthermore, the index 18 is made movable on the focal plane 5a and its size (distance) is also made changeable, so as to read by a micrometer or the like. On the basis of the above construction, as a blood vessel image (subject 36) and the index 18 are observed at the observation portion, by coinciding the index size with the blood vessel size, the blood vessel size can be obtained from both the magnifications and the value of the micrometer. As shown in FIG. 7b, it is also possible to provide the index 18 constructed as described above on a focal position 39 of the objective lens 2 and to form an image of the index together with the subject 36 (blood vessel image) on the focal plane 5a of the camera tube 5 by a relay lens 40. Moreover, in FIG. 6, a tilting mechanism is provided at the holding portion of the microscope device 1' so as to freely change the angle of the objective lens 2. Furthermore, in the above embodiment, the blood vessel image is magnified and projected as a color image, but if the color of a blood vessel or blood is not observed, it can be constructed in monochrome. In addition, the size of a blood vessel can be measured with the eye by projecting the index having a scale on the screen of the receiver 12.

What is claimed is:

1. An angioscope comprising a camera tube device having a reflection type illumination device for illuminating a blood vessel, an optical system for forming an image of the illuminated blood vessel and a photoelectric converting means for receiving said image of a blood vessel to generate an image signal of the blood vessel;
    a monitor means for receiving said image signal and displaying an image of the blood vessel on a screen by a known magnification;
    means for displaying an index on the screen of the monitor means in a superimposed manner with the image of the blood vessel;
    means for adjusting position and size of the index on the screen so as to make the index in correspondence with the image of the blood vessel;
    means for measuring the size of the index displayed in the screen to derive a size signal; and
    means for receiving said size signal and calculating an actual size of the blood vessel from the size signal and said magnification.

2. An angioscope comprising a camera tube device having a reflection type illumination device for illuminating a blood vessel, an optical system for forming an image of the illuminated blood vessel and a photoelectric converting means for receiving said image of blood vessel to generate an image signal of the blood vessel;
    a monitor means for receiving said image signal and displaying an image of the blood vessel on a screen by a known magnification;
    means for measuring a time required for a red blood cell in the blood vessel displayed on the screen, travelling over a predetermined distance; and
    means for receiving said time and calculating a flow rate of blood through the blood vessel from said time and said magnitude.

3. An angioscope comprising a camera tube device having a reflection type illumination device for illuminating a blood vessel, an optical system for forming an image of the illuminated blood vessel and a photoelectric converting means for receiving said image of blood vessel to generate an image signal of the blood vessel;
    a monitor means for receiving said image signal and displaying an image of the blood vessel on a screen by a known magnification;
    means for displaying an index on the screen of the monitor means in a superimposed manner with the image of the blood vessel;
    means for adjusting position and size of the index on the screen so as to make the index in correspondence with the image of the blood vessel;
    means for measuring the size of the index of displayed on the screen to derive a size signal; and
    means for receiving said size signal and calculating an actual size of the blood vessel from the size signal and said magnification;
    means for measuring a time required for a red blood cell in the blood vessel displayed on the screen, travelling over a predetermined distance; and
    means for receiving said measured time and calculating a flow rate of blood through the blood vessel from the time and magnification.

4. The angioscope as claimed in claim 3, wherein the size measuring index consists of two arrows arranged to face each other in a vertical straight line and said size of the blood vessel is measured as a distance between the heads of said arrows.

5. The angioscope as claimed in claim 1 or 3, wherein the size measuring means comprises a frame memory, the size of the index projected on the screen is read out of the frame memory.

6. The angioscope as claimed in claim 1 or 3, wherein said magnification of the image of blood vessel displayed on the screen is made variable.

7. The angioscope as claimed in claim 2 or 3, wherein the time measuring means comprises a measuring terminal having two light receiving elements arranged to separate by the predetermined distance, the measuring terminal is contacted onto the image displayed on the screen to detect a time required for the red blood cell travelling between the light receiving elements.

8. The angioscope of claim 2 further including a size measuring index displayed on the screen by means for displaying an index, said size measuring index being adjustable so as to be superimposed with the image of the blood vessel, said size measuring index consisting of two arrows arranged to face each other in a vertical straight line whereby the size of the blood vessel is measured as a distance between the heads of said arrows.

9. An angioscope for ascertaining measurements relating to a blood vessel, comprising:
    means forming a base;
    viewing means for observing a blood vessel, said viewing means comprising means for illuminating a blood vessel, and means for observing a blood vessel;
    video means for converting the image observed into an electronic image signal;
    displaying means for electronically displaying said blood vessel onto a visual screen electrically connected with said video means, said displaying means further comprising monitor means for receiving an image signal from said video means and displaying an image of a blood vessel with a predetermined magnification and means for measuring a characteristic of blood transmission through a blood vessel based at least in part on a measured distance across said image,
    whereby when said blood vessel is displayed by said displaying means and said measuring means operates to detect and display a measurement relating to the transmission of blood through a blood vessel.

10. The angioscope of claim 9 wherein said video means includes camera means for electronically observing a blood vessel for electronic transmission of an image signal to said displaying means.

11. The angioscope of claim 9 wherein said observing means includes means or physically viewing a blood vessel.

12. The angioscope of claim 10 wherein said displaying means further comprises means for projecting an image of an index on said displaying means, and means for adjusting the position and size of said image of an index, said means for measuring comprises means for measuring the size of the index projected, and said displaying means further comprises means for transmitting the measured size ascertained by said measuring means and the magnification of said monitor means, means for receiving the measured size ascertained by said measuring means along with the magnification of said monitor means, means for calculating an actual size of a blood vessel operationally associated with said receiving means based on the measured size and magnification, and means for showing the result, whereby a blood vessel is projected on said screen along with an adjustable index and is measured based on the adjustment of said index and the magnification of a blood vessel image.

13. The angioscope of claim 9 or 10 wherein said observing means comprises an objective lens.

14. The angioscope of claim 9 or 10, or 12 wherein said measuring means comprises means for measuring a time required for a red blood cell in a displayed blood vessel image to travel a predetermined distance, and means for receiving said time and calculating a flow rate of blood through a blood vessel from said time and the magnitude of the predetermined distance travelled.

15. The angioscope of claim 14 wherein said measuring means further includes light receiving means operatively associated with the image of a blood vessel on said displaying means, each of light receiving means being positioned so as to sense the passage of a blood cell through a blood vessel and located a predetermined distance apart.

16. The angioscope of claim 15 wherein said means for receiving said time and calculating a flow rate comprises a trigger pulse generator, flip flop means for receiving trigger pulses from said trigger pulse generator, clock pulse generator means for generating timed pulses, means forming a gate operatively connected to said clock pulse generator means and said flip flop means, means forming a counter electrically connected to said gate means, arithmetic means for calculating a flow rate electrically connected with said counter means and rate display means for displaying the output of said arithmetic means, whereby the outputs of said light receiving means are converted to trigger pulses by said trigger pulse generator means which trigger said flip flop means in alternating fashion, the output of said flip flop means forming an input to said gate means wherein the clock pulses of said clock pulse generator are gated by said output of said flip flop means such that the input of said arithmetic means comprises clock pulses for a duration of time dependent upon the output of said light receiving means, said rate display means being electrically connected to said arithmetic means to thereby visually display the output of said arithmetic means.

* * * * *